(12) United States Patent
Heimberger

(10) Patent No.: US 6,908,429 B2
(45) Date of Patent: Jun. 21, 2005

(54) SUCTION VALVE FOR A MEDICAL INSTRUMENT

(75) Inventor: Rudolf Heimberger, Oberderdingen (DE)

(73) Assignee: Richard Wolf GmbH, Knittlingen (DE)

( * ) Notice: Subject to any disclaimer, the term of this patent is extended or adjusted under 35 U.S.C. 154(b) by 11 days.

(21) Appl. No.: 10/376,035

(22) Filed: Feb. 27, 2003

(65) Prior Publication Data

US 2003/0181786 A1 Sep. 25, 2003

(30) Foreign Application Priority Data

Mar. 1, 2002 (DE) .......................................... 102 09 124

(51) Int. Cl.⁷ ................................................ A61B 1/12
(52) U.S. Cl. ...................................................... 600/159
(58) Field of Search ........................... 600/159; 604/6.1, 604/33, 99.01–99.04, 167.03–167.04, 167.06

(56) References Cited

U.S. PATENT DOCUMENTS 5,257,773 A * 11/1993 Yoshimoto et al. ......... 251/339
5,322,263 A 6/1994 Yoshimoto et al.
6,569,120 B1 * 5/2003 Green et al. ............ 604/167.04

FOREIGN PATENT DOCUMENTS

| DE | 29 54 069 C2 | 1/1984 |
| DE | 3441075 A1 | 6/1985 |
| EP | 0 106 310 | 1/1968 |
| GB | 2 149 884 A | 6/1985 |
| JP | 2001346761 A | 6/2000 |

* cited by examiner

Primary Examiner—Beverly M. Flanagan
(74) Attorney, Agent, or Firm—Cohen, Pontani, Lieberman & Pavane

(57) ABSTRACT

A suction valve for an instrument includes a valve insert secured in a valve housing. A first sleeve connects the interior of the valve housing to a first suction channel of the instrument; and a sealing membrane seals a first portion of the interior of the valve housing from the valve insert. The sealing membrane is fixed in the valve housing by the valve insert that includes a valve plunger for opening and closing the sealing membrane by movement in a first direction.

29 Claims, 4 Drawing Sheets

SUCTION VALVE FOR A MEDICAL INSTRUMENT

PRIORITY CLAIM

This application claims priority to DE 102 09 124.2 filed on Mar. 1, 2002 in Germany.

FIELD OF THE INVENTION

The invention relates to a suction valve for an endoscope. In particular, the invention relates to a suction valve coupled to an endoscope, an endoscope with a suction valve as well as to an associated valve insert.

BACKGROUND OF THE INVENTION

Suction valves which can be manually actuated via a push button are used in endoscopes, fiberscopes and other medical instruments to evacuate body secretions, irrigation fluid, or likewise from body cavities.

The suction valves disclosed in DE 29 54 069 C2 and EP 0 106 310 B1 have complicated structures since they must be gas-tight and liquid-tight. The valves include actuation elements which are designed like pistons and sealed to the housing by O-rings or similar. The O-rings are arranged on the piston-like actuation elements and at the same time are displaced axially within the valve housing. This arrangement causes friction and eventually leakage of the valves due to friction. Further, a disadvantage with these complicated valves is that they cannot be cleaned sufficiently or cleaned only with much effort. Additionally, they are expensive and time-consuming to manufacture.

SUMMARY OF THE INVENTION

It is an object of the invention to create a simplified suction valve which can be manufactured more economically and which is easier to clean. It is a further object of the invention to provide an endoscope with a simplified suction valve.

These and other objects are achieved by a suction valve for an instrument that includes a valve insert secured in a valve housing. A first sleeve connects the interior of the valve housing to a first suction channel of the instrument; and a sealing membrane seals a first portion of the interior of the valve housing from the valve insert. The sealing membrane is fixed in the valve housing by the valve insert that includes a valve plunger for opening and closing the sealing membrane by movement in a first direction.

The suction valve of the present invention is designed for an endoscope. However, within the context of the invention other medical apparatus where a manual opening of a fluid conduit, for example fiberscopes, is advantageous may be regarded as endoscopes. The suction valve of the patent invention includes a valve housing having a connection to a suction channel of an endoscope. A fluid to be suctioned away or to be conveyed enters through an entry of the connection into the suction valve. A sealing membrane with slits is arranged in the inside of the valve housing above the entry opening. This sealing membrane seals the suction conduit lying in front of the entry opening preferably in a fluid-tight and gas-tight manner. For opening the sealing membrane is widened in the region of the slits, in particular folded up in order to permit an entry of fluid into the suction valve. The sealing membrane is fixed in the valve housing by a valve insert. A valve plunger movable transversely, i.e. in particular perpendicularly to the sealing membrane for opening the sealing membrane, is arranged in the valve insert. To open the valve, the valve plunger presses against the sealing membrane so that the regions adjacent to the slit are deflected out or folded up so that an opening in the sealing membrane is created. The sections of the sealing membrane are deflected out preferably counter to the flow direction of the fluid to be suctioned. When closed, the sealing membrane preferably bears on the end-face of the valve insert or of the valve plunger. This has the advantage that the movable parts of the sealing membrane may be pressed against the valve plunger by the fluid pressure when the valve is closed. By way of the valve insert or the valve plunger a deflection of the movable parts of the sealing membrane is prevented in the flow direction of the fluid, so that the valve permits a pressure-tight closure of a suction conduit.

The sealing membrane is preferably designed elastically, for example from a polymer. This has the effect that the sealing membrane on opening or its deflection builds up a restoring force, which on release of the valve plunger moves this again back into its original position. This allows additional restoring elements, for example springs, to be done away with. The valve insert which serves for holding and guiding the valve plunger is secured in the valve housing with a non-positive and/or positive fit. In this manner the valve insert assumes a double function; one it guides the valve plunger and second it fixes the sealing membrane within the valve housing. This permits a simple construction of the suction valve since essentially only four components are necessary, the valve housing, the valve insert with the valve plunger and the sealing membrane. This creates a valve that is simple and inexpensive to manufacture and permits easy disassembly of the valve for cleaning.

An outlet is disposed on the valve insert and engages the valve housing to situate the valve insert per se a positive fit with the valve housing. The outlet connects a suction or fluid conduit to the valve, wherein the conduit evacuates the fluid further. The connection terminal also fixes the valve insert in the valve housing. Advantageously, the outlet may be releasably engaged with the valve housing so that the valve insert may be easily released again from the housing in order to disassemble the whole suction valve, for example for cleaning. Further, this permits easy replacement of the sealing membrane since it is only fixed in the valve housing by the valve insert.

Preferably, the valve housing comprises a cylindrical, or circular-cylindrical interior, wherein the entry opening is provided on a first end-face of the valve housing and the opposed end-face of the housing is designed open for inserting the valve insert. The valve insert includes a cylindrical, in particular circular-cylindrical shape contour corresponding to the inner space. This design permits the valve insert to be able to be held in the valve housing in a secured manner. By way of the openly formed side of the valve insert the valve insert may be applied into this in the longitudinal direction of the valve housing. The circular-cylindrical design permits a rotation of the valve insert in the valve housing for its securement.

It is further preferred that the sealing membrane has an outer shape that mates to the cross section of the interior of the valve housing and extends transverse to the longitudinal axis of the valve housing. This design permits the sealing membrane to bear essentially on the one end-face of the valve insert. Further, it is fixed in the interior in the radial direction, since it comprises an outer contour, in particular an outer diameter which corresponds to the inner contour or the inner diameter of the valve housing.

The sealing membrane preferably includes two slits which intersect and which extend through the sealing membrane's depth. This means the slits connect the two planar surfaces of the sealing membrane which are preferably parallel to one another. With the crossed arrangement of two slits one is able to create four pie-shaped movable sections in the center or in the inside of the sealing membrane. These movable sections serve as flaps which are deflected in order to open the sealing membrane or the suction valve. For this the valve plunger presses against these movable parts of the sealing membrane which are limited by the slits and deflect these out of the plane of the membrane creating an opening. With an elastic design of the membrane, these movable sections or flaps on releasing the pressure move through the valve plunger back into their original position. The flaps with their end-face edges, i.e. the side surfaces of the slits, abut one another and completely seal the passage.

In a preferred embodiment form the sealing membrane in its center has a greater thickness than in its circumferential region. This design creates a greater strength of the sealing membrane which leads to an improved sealing. Furthermore a greater restoring force of the membrane or the movable sealing membrane parts may be achieved.

It is even more preferred for at least the center region of the sealing membrane to be designed conically. With this design preferably one side of the membrane is designed planar, whilst the other elevates to the middle of the sealing membrane in a cone. The planar side of the membrane usefully faces the valve plunger in order in the closed condition to come into bearing with this.

The crossing point of the at least two slits in the sealing membrane usefully lies in the region of the largest thickness of the sealing membrane. With this arrangement the design of the sealing membrane with an increasing thickness, in particular the conical design of the sealing membrane, has the effect that the side surfaces bearing on one another in the direction of the thickness of the membrane have a large as possible length. In this manner a large as possible bearing surface is created between the movable sections of the membrane in order to achieve a more reliable sealing. The oblique or conical course of the membrane thickness is advantageously selected such that the membrane has the least thickness in the region in which the deformation for deflecting or folding up the membrane is effected. At the same time the actuation forces for opening the suction valve, i.e. for moving the movable membrane parts may be kept small.

In a further preferred embodiment form, on the surface of the sealing membrane which faces the valve plunger there is formed a centrical, preferably conical recess. This recess extends into the inside of the sealing membrane, but however not through this. The recess effects an increase of the passage opening created on opening the valve, since on account of the oblique or conical design of the recess less material projects into the passage opening and thus into the flow path. In this manner one may create a large passage opening with a minimal stroke of the valve plunger.

The sealing membrane is preferably clamped in its circumferential region between a shoulder in the valve housing and an end-face of the valve insert. For this an annular shoulder or step may be formed in the valve housing, on which shoulder or step the membrane comes to bear in its entire circumferential region so that one achieves a secure sealing between the sealing membrane and the valve housing. On its opposed side the sealing membrane likewise preferably with its entire circumferential region bears on the end-face of the valve insert so that a uniform pressing force acts on the sealing membrane. The inner region or preferably the middle region of the sealing membrane is preferably freely movable through the valve plunger in order to permit a simple opening and closing of the sealing membrane. Advantageously, the valve housing is formed cup-like, wherein the entry opening is formed in the base. In the periphery of the inner space there is formed a bearing shoulder on which the sealing membrane bears if the valve insert is applied into the cup-like valve housing and is connected to this, so that the sealing membrane is fixed on the base of the valve housing over the entry opening.

On the surface of the sealing membrane that faces the valve plunger, an annular groove that is radially outside the slots is disposed. The slits are thus arranged completely within the surface enclosed by the annular groove. The annular groove serves for decoupling the elastically deflectable flap between the slots from the edge region of the sealing membrane, which is tensioned between the housing and the valve insert. By way of this so-called decoupling it is achieved that on adding the valve insert into the valve housing the elastic deformations of the sealing membrane caused by friction on the one hand and by compression deformation on the other hand are not transmitted to the flaps limited by the slots. Thus, on applying and clamping in the sealing membrane one prevents a deformation of the flaps as well as a change of the slits located between the flaps, and thus a negative impairment of the sealing effect.

The outlet extends preferably transverse to the longitudinal axis of the valve housing and the entry opening. This means that the outlet extends radially away from the valve insert. This arrangement permits a discharge tubing to be connected to the valve in a manner such that it does not hinder an operator too much on actuation of the suction valve. Further, such an outlet is suitable for simultaneously fixing the valve insert in the valve housing. A fixation of the valve insert in the valve housing is required particularly in the longitudinal direction, i.e. in the actuation direction of the valve plunger. In order to achieve this fixation the outlet may be hooked into a corresponding recess in the valve housing or engage behind a corresponding projection in the valve housing. In this manner one may do away with additional fastening elements for fixing the valve insert in the valve housing, by which means the number of required individual parts is minimized and the manufacture is simplified. For example, the valve insert with an outlet that is angled may be connected to the valve housing in the manner of a bayonet closure, in that the valve insert is firstly moved in the longitudinal axis of the valve housing and then is rotated about this axis.

For this, preferably in the walling of the valve housing there is formed an L-shaped groove whose first area extends essentially parallel to the longitudinal axis and is open towards the edge of the valve housing, and whose second area runs transverse to the first section essentially in the circumferential direction of the valve housing, wherein the groove has a width which corresponds to the cross-sectional size, i.e. preferably to the diameter of the outlet. With such a valve housing the valve insert with the angled outlet is applied in the direction of the longitudinal axis of the valve housing such that the outlet is first moved through the area of the groove parallel to the longitudinal axis. If the valve insert is applied far enough, i.e. preferably completely in the longitudinal direction into the valve housing, the outlet has reached the start of the groove section running in the circumferential direction. This allows the valve insert now to be rotated about the longitudinal axis of the valve or of the valve housing, wherein the outlet in its angled position with respect to the longitudinal axis is moved through the part of the L-shaped groove running in the circumferential direction. If the outlet is completely in this area that is transverse or circumferential, the valve insert in the direction of the longitudinal axis is secured in the valve housing. In order to prevent an unintended rotating back of the valve insert in the L-shaped groove, in the area running in the circumferential direction there may be formed an additional recess or relief into which the outlet engages in order to prevent a rotation. This is ideally supported by the elastic design of the sealing membrane. On applying the valve insert into the valve housing the sealing membrane by way of the valve insert is pressed against the annular or bearing shoulder in the inside of the valve housing such that the sealing membrane is first slightly compressed. If the outlet has reached its final position in the L-shaped groove, i.e. the area of an additionally provided grooved area, then the sealing valve is relieved at least partly and presses the outlet into the relief, thus additionally securing the valve because of the spring effect of the sealing membrane.

The valve insert is preferably designed in a manner such that in the region of the longitudinal axis of the housing it comprises a passage hole or an inner space in which the valve plunger is movably arranged in the longitudinal direction, and a sleeve which opens in the radial direction towards the passage hole, wherein the valve plunger is formed tubular and on its side facing the sealing membrane comprises an entry opening and on its periphery comprises at least one radial opening which is in connection with the exit opening. For opening the valve, the valve plunger is pressed against the sealing membrane so that its movable parts are deflected out and an opening is released. At the same time the entry opening of the valve plunger faces the opening of the sealing membrane so that a fluid may flow into the inside of the valve plunger and further through the radial opening in the valve plunger to the exit opening and through the outlet. This arrangement permits a very compact design of the suction valve since the flow path to be released is situated in the inside of the valve plunger. The inner space of the valve housing in the periphery of the valve plunger may additionally be widened in an annular manner so that an annular hollow space is formed, through which a fluid may flow from the radial opening in the valve plunger to the exit opening. By way of this arrangement one may make do without an exact positioning of the radial opening to the exit opening.

The end-face of the valve plunger that is distal to the sealing membrane is preferably designed as a closed pressure cap. In this manner a fluid to be suctioned away is prevented from being able to exit from the valve plunger at this side, and surrounding air is prevented from being aspirated at this location. The pressure cap simultaneously serves for actuating the valve plunger in that it may be moved in its longitudinal direction by finger pressure for opening the sealing membrane. In order to achieve a large pressure surface and a formation of the suction valve which is smooth towards the outside, the pressure cap on the upper side preferably covers the whole valve insert.

Additionally between the pressure cap and the valve insert one may arrange a sealing element which in the opened condition of the suction valve seals the passage hole or the inner space in the valve insert towards the pressure cap. The sealing element is preferably an O-ring which surrounds the valve plunger bordering the pressure cap. If the suction valve is in its opened position, i.e. the valve plunger is pressed completely into the valve insert, this sealing element or the O-ring comes into bearing with the upper or outer end-face of the valve insert or with circumferential edge of the passage hole of the valve insert and seals the inner space of the valve insert to the outside. By way of this it is achieved that a sealing at this location is effected only in the opened condition of the suction valve. If the suction valve is located in its closed position, the inner space of the valve insert at its side distant to the sealing membrane is not sealed by the sealing element so that "false air" is aspirated through the suction conduit which is constantly impinged by a vacuum. The valve insert with the valve plunger and the sealing membrane preferably form an exchangeable unit. This design allows the whole valve insert to be formed as a wearing or disposable part, which may be replaced after it has been used once. This spares the laborious cleaning of the suction valve. Furthermore the valve insert when worn may also be easily replaced without extensive repair work having to be carried out. All parts of the valve insert, i.e. likewise the valve plunger and the sealing membrane are preferably manufactured of plastic and preassembled, which permits an inexpensive large-scale production.

The movement possibility of the valve plunger within the valve insert is at the same time usefully limited by at least one abutment, i.e. preferably the position of the valve plunger in the upper, i.e. unactuated end position is limited by an abutment. A pressure cap may serve as a second abutment. The first abutment may be designed as a preferably annular latching projection on the valve plunger, said projection engaging on a corresponding inwardly directed annular shoulder in the inner space of the valve insert so that this may not inadvertently be pulled out of this, which could lead to an unintended opening of the suction valve during operation. Furthermore the valve plunger may neither become lost during storage and cleaning of the valve insert. The abutment or projection on the valve plunger may however be formed as a latching projection to such an extent that on applying a suitably large pulling force the valve plunger may again be removed from the valve insert in order e.g. to be able to clean or exchange the parts. For this the annular latching projection on the valve plunger may for example comprise at least one, preferably however several slot-like openings.

Preferably the at least one abutment is arranged on an elastic web formed on the valve plunger. In this manner the abutment may form an elastic latching projection which permits an insertion and release of the valve plunger into or out of the valve insert. If the force acting on the abutment exceeds the spring force of the web, the abutment is correspondingly deflected so that it may pass a corresponding latching projection formed in the valve insert or the corresponding annular shoulder in the valve insert. Preferably the elastic web is formed by a wall section of the valve plunger. If several passage holes are formed in the valve plunger such elastic webs may be formed by the wall sections lying between the passage holes. The required elasticity is set by the thickness and width of these wall sections. This design has the advantage that one does not need to apply additional spring elements, since the required spring effect is formed by narrow wall sections between the passage holes which are present in any case.

Furthermore on the periphery of the valve insert it is useful to form at least one projection which engages around the sealing membrane. For this, on that lower end of the valve insert which faces the sealing membrane there is formed an annular groove into which the sealing membrane engages. In this manner the sealing membrane may be held on the valve insert and be easily exchanged together with this.

The valve housing may be rigidly connected to the endoscope whilst the valve insert with the valve plunger and the sealing membrane is designed exchangeable and removable from the housing. In this way the number of individual parts which need to be dismantled for cleaning is minimized. For cleaning it is sufficient the remove the valve insert from the housing or to replace this with a new valve insert. If the valve insert for example is of metal then where appropriate only the exchange of the sealing membrane may be required.

The valve housing is furthermore preferably formed as one piece with at least one component of the endoscope, by which means the number of required individual parts to be assembled is further reduced.

The invention further relates to a valve insert belonging to the previously described suction valve, which for example may be offered in the form of a packaged unit as an exchange part. The valve insert comprises a passage hole or inner space which runs in the longitudinal direction and in which there is arranged a valve plunger movable in the longitudinal direction, and a radially extending connection terminal. The valve insert may together with the valve plunger be applied into the valve housing, wherein the radially extending connection terminal serves for locking the valve insert in the valve housing in the manner of a bayonet closure.

Preferably a sealing membrane is attached on one end-face of the valve insert, said sealing membrane being able to be opened by movement of the valve plunger. The opening and closing of the sealing membrane is effected in the above-described manner. The rigid arrangement of the valve membrane on the valve insert has the effect that all wearing parts and exchangeable parts of the valve together with the valve insert are integrated in a unit so that a simple exchange of the wearing parts is possible.

The valve plunger is preferably formed tubular and at one end-face comprises an entry opening as well as on its periphery at least one radial exit opening which is in connection with the outlet. The inside of the valve plunger may thus form a flow path so that as a whole a compact design of the valve insert and thus of the associated suction valve is achieved.

The end-face of the valve plunger which is opposed to the entry opening is preferably formed as a closed pressure surface. This surface serves for actuating the valve and is accordingly usefully formed particularly large in order to ensure a sufficiently large finger contact surface for a secure actuation of the valve.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

DESCRIPTION OF THE PRESENTLY PREFERRED EMBODIMENTS

Figure 1:
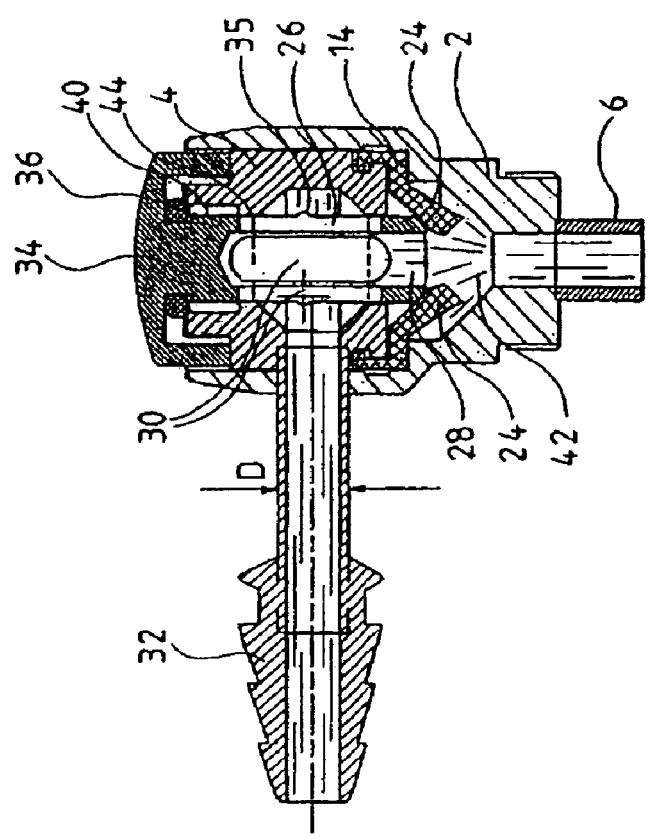
FIG. 1 is a longitudinal sectional view of the suction valve in the closed condition.

FIG. 1 shows a valve in accordance with the present invention when closed and pressure tight. The valve, which is preferably arranged at the proximal end of an endoscope (not shown), includes a valve insert 4 in valve housing 2. The valve housing 2 is connected to an endoscope or is integral with the endoscope. The valve housing 2 is essentially circular-cylindrical and at its end-face centrally includes sleeve 6 that is connected to an associated evacuation channel, for example a suction channel of an endoscope. The sleeve 6 opens into the interior 8 of the valve housing 2. The interior space 8 has a cylindrical shape and is open towards the second end-face 10 of the valve housing 2. The valve insert 4 is inserted into the valve housing 2 from the second end-face 10. A sealing membrane 14 is disposed on a shoulder formed on the periphery in the interior 8 of the valve housing 2 in the region of the side distant to the end-face 10.

The valve insert 4 is cylindrical and corresponds to the inner diameter of the valve housing 2. Thus, the valve insert 4 may be inserted into the valve housing 2 in a fitting manner and may be fixed in the valve housing 2 in the radial direction. The side of the valve insert 4 facing the sleeve 6 is formed planar and bears on the sealing membrane 14. The end of valve insert 4 opposite the sleeve 6 has a circumferential groove 16 which engages a circumferential edge 18 of sealing member 14. The sealing membrane 14 is designed essentially as a planar, round disk with a diameter corresponding to the inner diameter of the valve housing 2. At its periphery, the sealing membrane 14 has a projecting edge 18 which engages with a radially inwardly directed projection into the circumferential groove 16 of the valve insert 4. The sealing membrane 14 may therefore be clipped or snapped on the valve insert 4. Thus, it is held by the valve insert 4 and forms a unit with 17. The valve insert 4 with the sealing membrane 14 is applied into the valve housing 2 so that the sealing membrane 14 bears at its periphery completely on the step 12 in the valve housing 2 sealing the region of the interior 8 of the valve housing 2 which faces the connector 6.

Figure 5:
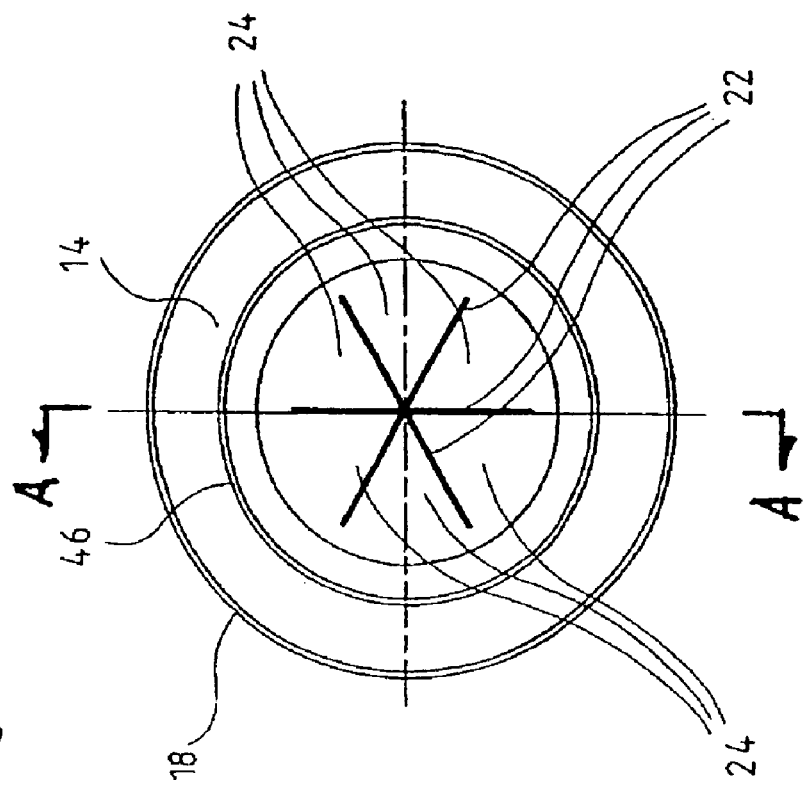
FIG. 5 is a plan view of the sealing membrane of the suction valve.

The side of sealing membrane 14 facing the sleeve 6 of the valve housing 2 has a cone 20 which has its highest point or its tip essentially in the center of the sealing membrane 14. As shown in FIG. 5, the sealing membrane 14 in its center region has three slits 22 which intersection point in the centre of the sealing membrane 14. The slots 22 extend through the sealing membrane 14 and connect the two surfaces of the sealing membrane 14 to one another. The crossing slits 22 form four pie-shaped flaps 24 whose free ends or tips face one another. These flaps 24 may be folded about an axis which connects two adjacent end points of the slits 22 to one another to release an opening in the center of the sealing membrane 14 and to open the valve. While three crossed slits 22 are shown, only two or more than three crossed slits may be provided, wherein the number of flaps 24 correspondingly changes.

The valve insert 4 is tubular, such that inner space of the valve insert 4 has a circular cross section. A valve plunger 26 is movably guided in the inside of the valve insert 4. The valve plunger 26 may be displaced in the longitudinal direction of the valve, i.e. in the direction of the longitudinal or middle axis of the valve insert 2 towards the sleeve 6. The valve plunger 26 is likewise tubular and the end opposite the sleeve 6 includes an entry 28. The edge of the valve plunger 26 which surrounds entry 28 bears on the surface of the sealing membrane 14. Furthermore, the valve plunger 26 comprises radial openings 30 that are open towards the inner space of the valve insert 4. The inner space of the valve insert 4 is widened in its center region into an annular channel which surrounds the valve plunger 26. This annular channel connects with the outlet 32. The outlet 32 extends radially to the valve insert 4 and the valve housing 2, a direction that is transverse to the sleeve 6.

The end of the valve plunger 26 distal to the sleeve 6 is a pressure cap 34. The pressure cap 34 extends on the end distant to the sleeve 6 over the entire end-face of the valve insert 4 to create a large pressure surface for actuating the valve. A sealing ring 36 is arranged below the pressure cap 34. When the valve is open, sealing ring 36 comes into bearing with the valve insert 4.

The valve insert 4 from the open end is applied into the cup-like valve housing 2. The outlet 32 engages into a groove 38 in the valve housing 2 in order to lock and to secure the valve insert 4 in the valve housing 2 in the manner of a bayonet closure. The outlet 32 is preferably securely connected to the valve insert 4 or is designed integral with the valve insert, for example when made of plastic. The valve plunger 26 is held in the inside of the valve insert 4 by circumferential, radially extending projections 35 or an annular projection 35 of the valve plunger 26. The projections 35 are arranged on the wall sections or webs remaining between the radial openings 30. These narrow webs between the openings 30 deflect elastically inwards, causing the projections 35 to move radially inwards. On removal of the valve plunger 26, the part-annular projections 35 arranged on the webs to be deflected by the ramp-like cross sectional narrowings 44 (see FIG. 2) towards the middle axis as soon as the valve plunger 26 has been retracted out of the valve insert 4 or been inserted into this. At the same time, the spring force of the webs on which the projections 35 are arranged must be overcome. Preferably, the valve plunger 26 is made of plastic and latches the projections 35 into the valve insert 4. Thus, the valve plunger 26, the valve insert 4, and the sealing membrane 14 fastened thereon form a unit which may easily be exchanged and may be held in the valve housing with the help of the outlet 32. The number of individual parts required for the valve at the same time is considerably reduced creating a very inexpensive, easily maintained valve whose wearing parts may very simply be replaced as a single unit. Thus, the valve may be easily opened or disassembled for cleaning.

The valve insert 4 distal to the sleeve 6 comprises a circumferential extension or enlargement open towards the outside, which is an annular space 40 that surrounds the valve plunger 26 and is connected with radial openings 30 in the valve plunger 26. When closed, the valve as shown in FIG. 1 has a flow path from the outlet 32 through the openings 30 and the annular space 40 towards the atmosphere to aspirate "false air" while the valve or the sealing membrane 14 are closed. This is useful if the outlet 32 is connected to a continuously acting vacuum source.

When closed, the valve has a good sealing effect since the vacuum produced in the valve insert 4 as well as the restoring forces caused by the elastic design of the sealing membrane 14 is held in its position bearing on the end-face of the valve insert 4. Thus, the slits 22 in the sealing membrane 14 are held sealingly closed. At the same time, the conical design of the sealing membrane 14 creates large bearing surfaces or side surfaces in the slits 22 which improve the sealing effect and the restoring force of the sealing membrane 14. An invasion of the movable flaps 24 of the sealing membrane 14 into the inside of the valve insert 4 is securely prevented even at high pressures sealing membrane 14 bearing on the circumferential edge of the valve plunger 26 and the end-face of the valve insert 4 and by the conical design of the sealing membrane 14.

Figure 2:
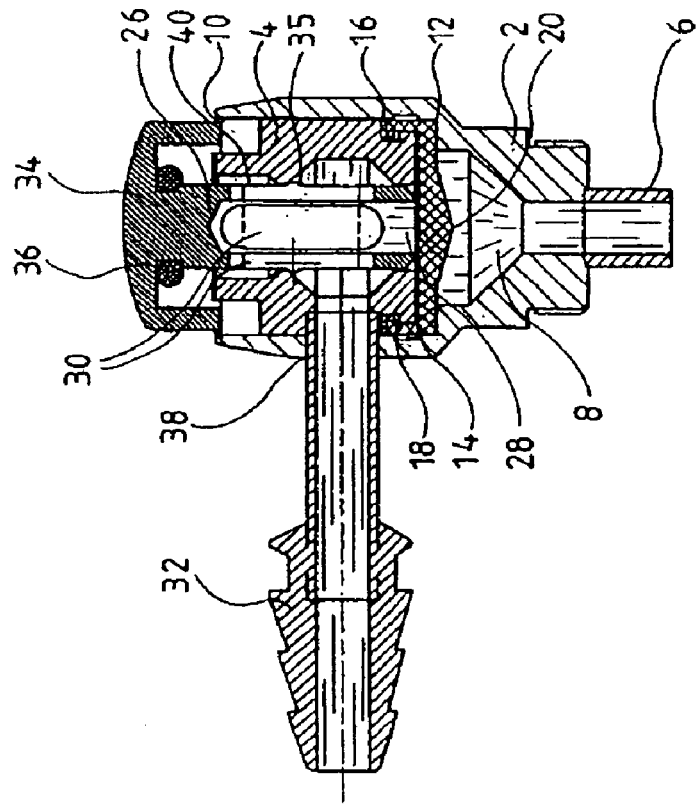
FIG. 2 is a longitudinal sectional view of the suction valve in the open condition.

FIG. 2 shows the valve of FIG. 1 when opened. To open the valve, the pressure flap 34 including the valve plunger 26 are pressed into the valve insert 4 toward the sleeve 6. At the same time, the sealing ring 36 below the pressure flap 34 bears a valve insert 4 and closes the annular space 40 so that aspiration of air from the atmosphere is stopped.

The end of the valve plunger 26 opposite to the pressure cap 34 presses against the movable flaps 24 of the sealing membrane 14 so that these fold up in the direction of the connection terminal 6 and create an opening in the sealing membrane 14. For an easy opening of the flaps 24, the circumferential edge of the valve plunger 26 surrounding the opening 28 is chamfered or bevelled at its radial outer side. The opening of the sealing membrane 14 releases a flow path via the opening 42, the opening 28 and the openings 30 in the valve plunger 26 toward the outlet 32 so that a fluid may be suctioned out through the valve via a suction channel connected to the connection terminal through the valve.

To close the valve the pressure flap 34 is released. Thus, the valve plunger 26 moves back into its original position shown in FIG. 1 because of the restoring force of the elastically designed sealing membrane 14 and the vacuum acting on the sealing membrane 14. At the same time, the movement of the valve plunger 36 is limited by the radial projections 35 which bear on a cross sectional narrowing 44 in the inside of the valve insert 4.

Figure 3:
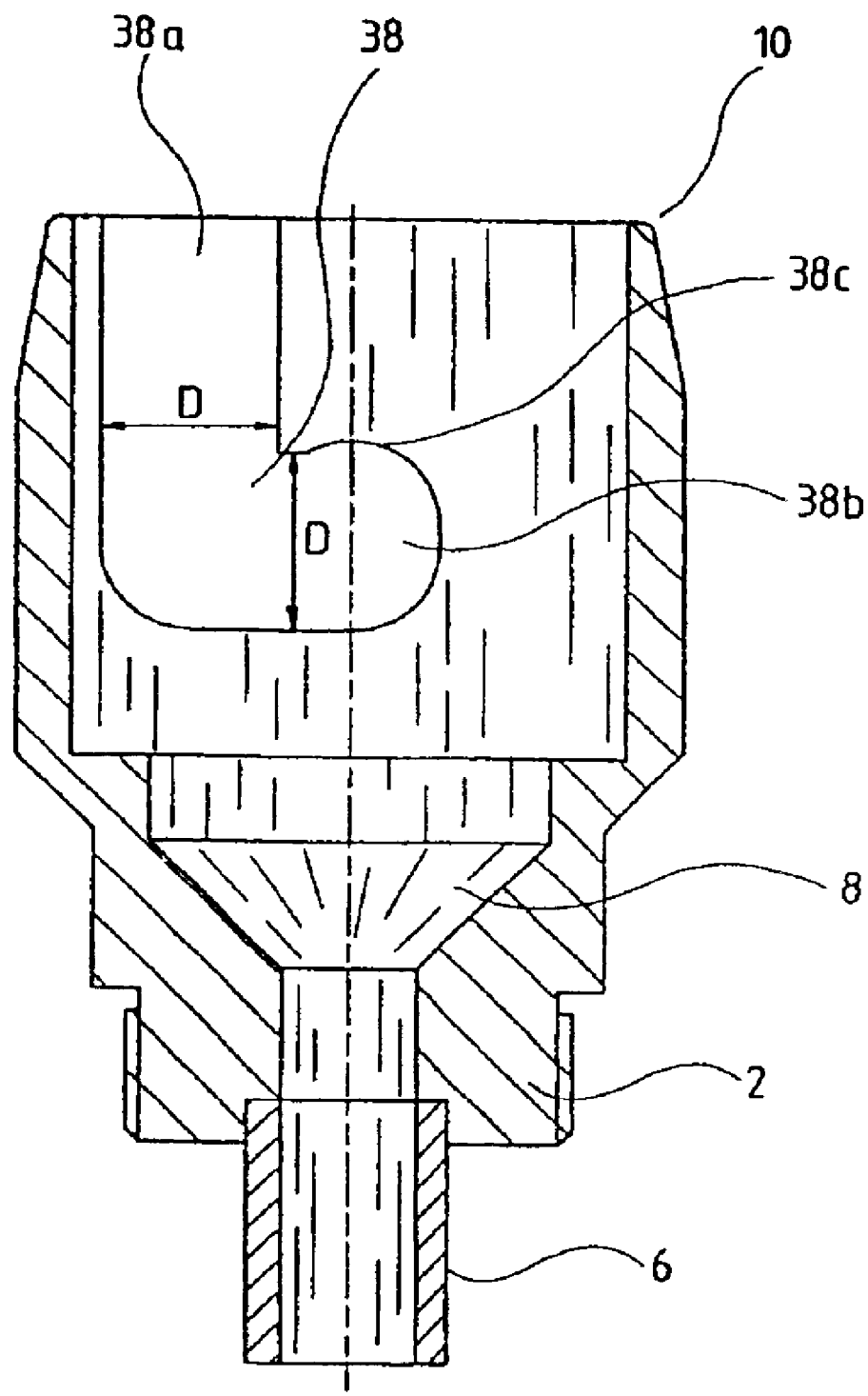
FIG. 3 is a longitudinal sectional view of the valve housing.

FIG. 3 shows a sectional view of the valve housing 2 shown FIGS. 1 and 2. The sleeve 6 is fastened or designed at the bottom end of the valve housing 2. The valve insert 4, not shown in FIG. 3, is inserted into the valve housing 2 from the top end. A groove 38 is formed in the circumferential wall of the valve housing 2. The groove 38 is open towards the end-face 10 and includes two areas 38a and 38b. Area 38a extends parallel to the longitudinal axis of the valve insert 2, i.e. perpendicular to the circumferential edge on the end-face 10, and is open towards the end-face 10. Area 38b extends transversely to area 38a in the circumferential direction of the valve housing 2. The groove 38 with areas 38a and 38b have a width that corresponds to the diameter D (see FIG. 2) of the outlet 32. (See FIGS. 1 and 2.) This allows the outlet 32 to be guided into groove 38 on inserting the valve insert 4 into the valve housing 2.

To insert the valve insert 4 into the valve housing 2, the outlet 32 is guided first by area 38a of the groove 38 so that the valve insert 4 may only be moved in only one direction parallel to the longitudinal axis of the valve housing 2, specifically in the direction of the sleeve 6. If the outlet 32 comes into the region of the transverse area 38b of the groove 38, the valve insert 4 with the outlet 32 in the valve housing 2 may be rotated about the longitudinal axis of the valve housing 2, wherein the outlet 32 is moved through the area 38b of the groove 38. The outlet 32 at the same time pivots in its angular position with respect to the longitudinal axis of the valve housing 2 and of the valve insert 4.

The transverse area 38b includes a recess 38c at its end. Recess 38c is a bulge upwards in the direction parallel to the longitudinal area 38a. Recess 38c secures valve insert 4 rotationally to the outlet 32. To insert the valve insert 4 into the valve housing 2 the valve insert 4 is pressed against the sealing membrane 14 elastically deforming the membrane 14 under compression. Subsequently, the valve insert 4 is rotated in the valve housing 2 until the outlet 32 reaches the end position of the transverse area 38b. In this position, the pressure on the valve insert 4 against the sealing membrane 14 is released. In turn, the outlet 32 is pressed into the recess 38c at the end of the area 38b because of the elastic restoring force of sealing membrane 14. The valve insert 4 is secured against rotation by engaging the outlet 32 into the recess 38c. To release the valve insert 4, it is again pressed against the sealing membrane 14 so that it is elastically deformed in compression. Thus, the outlet 32 is disengaged from recess 38c, so that the valve insert 4 may be rotated further and then removed from the valve housing 2.

Figure 4:
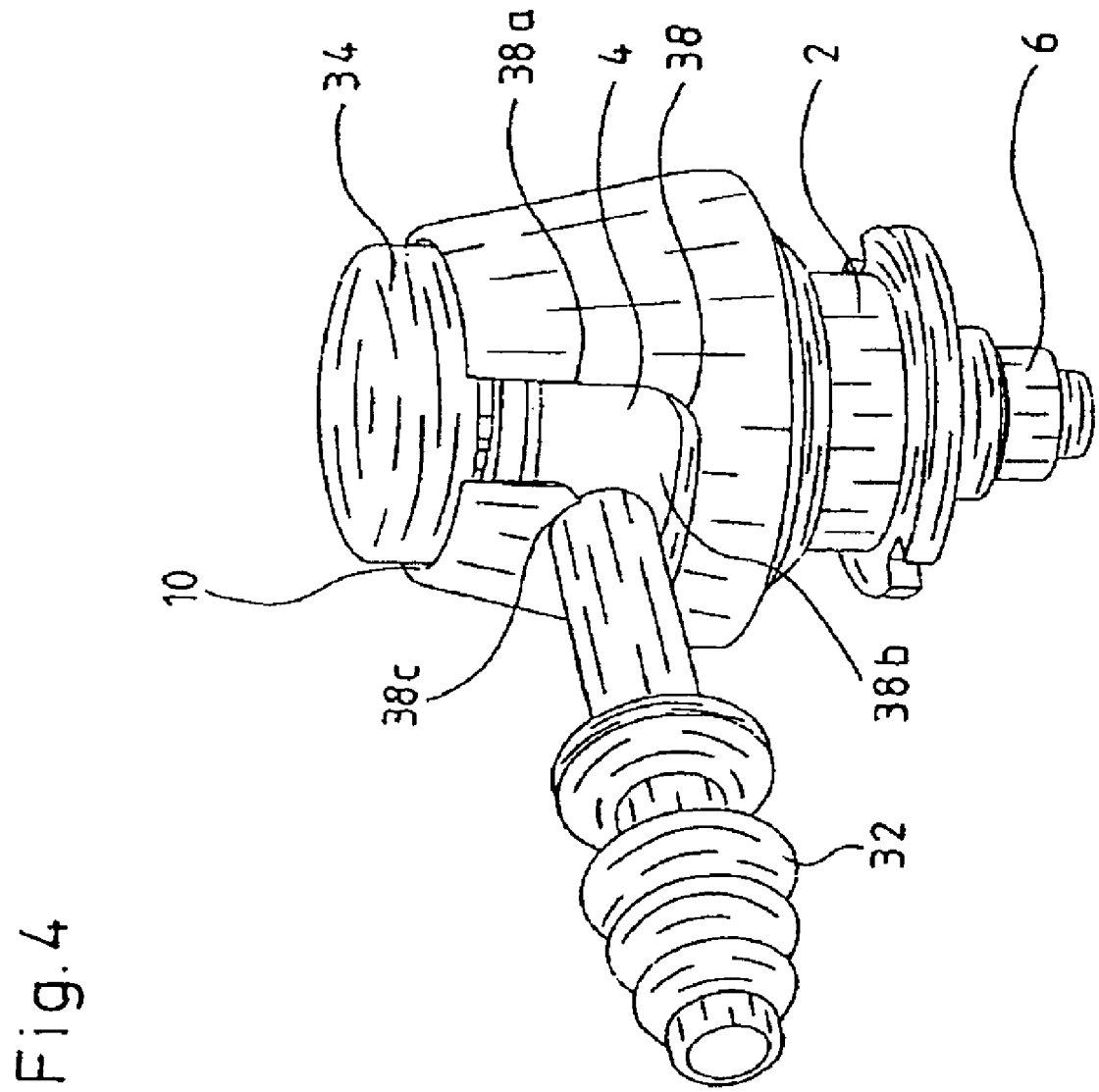
FIG. 4 is a perspective view of the suction valve.

FIG. 4 is a perspective entire view of the valve and illustrates the previously described securing of the valve insert 4 in the valve housing 2 in the manner of a bayonet closure. As shown in FIG. 3, the area 38a of the groove 38 extends parallel to the longitudinal axis of the valve or of the valve housing 2, while area 38b of the groove 38 extends in the circumferential direction through the wall of the valve housing 2. The outlet 32 extends through the groove 38 and secures the valve insert 4 in the axial direction in the valve housing 2. The outlet 32 thus assumes a double function; first connecting a suction tube and second securing the valve insert 4 in the valve housing 2.

Figure 6:
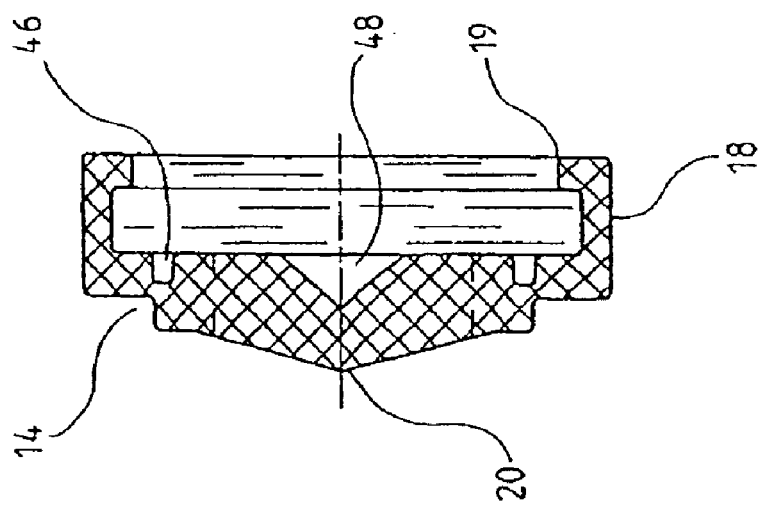
FIG. 6 is a cross-sectional view of a sealing membrane of the suction valve at line A—A of FIG. 5.

FIG. 6 is a cross-sectional view at line A—A of the sealing membrane 14 shown in FIG. 5. The sealing membrane 14 is formed cup-like, i.e. at its outer periphery. It includes an edge 18 projecting perpendicular to the surface of the sealing membrane 14. At the outer edge, the edge 18 includes a radially inwardly directed annular projection 19 which fastens the sealing membrane 14 on the valve insert 4 by engaging into the circumferential groove 16 on the valve insert 4. The side of the sealing membrane 14 distal to valve plunger 26, i.e. the side facing the sleeve 6, is conically shaped. Cone 20 formed on this surface of the sealing membrane 14 has its tip or its highest point in the center of the sealing membrane 14 at essentially the intersection point of the slits 22 as shown in FIG. 5. On the opposite side of cone 20, sealing membrane 14 has a conical recess 48. While this design is a preferred embodiment, it is not a required feature. Thus, the sealing membrane 14 shown in FIGS. 1 and 2 does not include recess 48. Recess 48 has the effect that the flaps 24 are open (see FIG. 5) it allows for a larger passage opening since less material protrudes into the flow path.

Further, the sealing membrane 14 shown in FIG. 6 includes an annular groove 46 on the surface which faces the valve insert 4. Groove 46 also is a preferred design which is not required with the sealing membrane 14 shown in FIGS. 1 and 2. The annular groove 46 near the valve circumference is disposed on the side of the sealing membrane 14 which faces the valve insert 14, i.e. it extends in the vicinity of the edge 18 lying radially further inwards and parallel to this. The annular groove 46, as is to be seen in FIG. 5, runs outside the slits 22 which are completely arranged in the region enclosed by the annular groove 46. Preferably the ends of the slits 22 are distanced radially inwards from the annular groove 46. The annular groove 46 serves for decoupling the flaps 24 defined by the slits 22 from the outer, edge region of the sealing membrane. With the edge region of the sealing membrane 14 is constrained or clamped between the valve insert 4 and the valve housing 2. At the same time stresses are produced in the inside of the sealing membrane 14. The annular groove 46 has the effect that the flaps 24 on clamping the sealing membrane 14 in the valve housing 2 are not influenced by stresses. Thus, slits 22 and flaps 24 retain their predefined shape and a reliable sealing and a defined opening of the sealing membrane 14 is possible.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A suction valve for an instrument, comprising:
   a valve insert secured in a valve housing;
   a first sleeve for connecting the interior of the valve housing to a first suction channel of the instrument;
   a sealing membrane for sealing a first portion of the interior of the valve housing from the valve insert, the sealing membrane fixed in the valve housing by the valve insert, the valve insert including a valve plunger for opening and closing the sealing membrane by movement in a first direction; and
   an abutment on an elastic web surrounding the valve plunger, the abutment operably interacting with the valve insert for limiting the movement of the valve plunger.

2. The suction valve of claim 1, where the movement in the first direction is substantially perpendicular to an axis of the sealing membrane.

3. The suction valve of claim 1, further comprising:
   a second sleeve secured in the valve housing for connecting the valve insert with a second channel.

4. The suction valve of claim 1, wherein the valve housing further comprises a substantially cylindrical interior including one end for inserting the valve insert, and one end disposed with an opening for operably connecting the interior to the first sleeve.

5. The suction valve of claim 4, wherein the exterior shape of the valve insert substantially mates with the interior of the valve housing.

6. The suction valve of claim 1, wherein the sealing membrane substantially mates with a cross-section of the valve housing.

7. The suction valve of claim 1, wherein the sealing membrane further comprises intersecting slits for dividing the sealing membrane.

8. The suction valve of claim 1, wherein the sealing membrane is thicker in the center than near the edge.

9. The suction valve of claim 8, wherein a first side of the sealing membrane is substantially conical.

10. The suction valve of claim 8, wherein the slits are disposed at least in the center of the sealing membrane.

11. The suction valve of claim 1, wherein a second side of the sealing membrane has a substantially conical recess.

12. The suction valve of claim 1, wherein the periphery of the sealing membrane is disposed between a shoulder of the valve housing and the valve insert.

13. The suction valve of claim 1, wherein slits are disposed interior to an annular groove on a side of sealing membrane proximal to the valve plunger.

14. The suction valve of claim 2, wherein the second sleeve is transverse to a longitudinal axis of the valve housing.

15. The suction valve of claim 1, wherein the valve housing further comprises a groove for securing the valve insert in the valve housing.

16. The suction valve of claim 15, wherein the groove comprises a first area substantially parallel to the longitudinal axis of the valve housing and open toward an edge of the valve housing, and a second area substantially transverse to the first area in the circumferential direction of the valve housing.

17. The suction valve of claim 15, wherein the groove has a width that corresponds to the cross-section of an outlet terminal secured in the valve housing for connecting the valve insert with a second channel.

18. The suction valve of claim 1, wherein the valve insert in the direction of the longitudinal axis of the valve housing further comprises:
   a passage hole for moving the valve plunger in the longitudinal direction, and
   an exit for opening in a radial direction toward the passage hole; wherein
   the valve plunger is tubular and at a first side faces the sealing membrane and comprises an entry opening and at least one radial opening on the periphery for connecting with the exit.

19. The suction valve of claim 1, wherein the valve plunger further comprises a closed pressure cap at a distal end from the sealing membrane.

20. The suction valve of claim 19, further comprising a sealing element disposed between the pressure cap and the valve insert, the sealing element for opening and closing a passage hole in the valve insert.

21. The suction valve of claim 1, wherein the valve insert, the valve plunger, and the sealing membrane are an exchangeable unit.

22. The suction valve of claim 1, wherein the interior of the valve insert further comprises an abutment for limiting the movement of the valve plunger.

23. The suction valve of claim 1, the valve insert further comprises a projection on the periphery of the valve insert for engaging the sealing membrane.

24. An instrument comprising:
   an endoscope,
   a suction valve rigidly connected to the endoscope, the suction valve comprising
   a valve insert secured in a valve housing;
   a first sleeve for connecting the interior of the valve housing to a first suction channel of the instrument;
   a sealing membrane for sealing a first portion of the interior of the valve housing from the valve insert, the sealing membrane fixed in the valve housing by the valve insert, the valve insert including a valve plunger for opening and closing the sealing membrane by movement in a first direction; and
   an abutment on an elastic web surrounding the valve plunger, the abutment operably interacting with the valve insert for limiting the movement of the valve plunger.

25. The instrument of claim 24, wherein the valve housing is integral with a part of the endoscope.

26. A valve insert for a suction valve, comprising:
   a body defining an inner space and a main axis;
   a valve plunger for moving in a direction longitudinal to the main axis of the body of the valve insert under a pressure, the valve plunger having an abutment on an elastic web surrounding the valve plunger, the abutment operably interacting with the tubular body of the valve insert for limiting the movement of the valve plunger,
   a passage hole longitudinal to a main axis of the body of the valve insert for passing the pressure, and
   a radially extending sleeve for evacuating the pressure.

27. The valve insert of claim 26, further comprising a sealing membrane disposed on the end of the valve insert for opening and closing by the valve plunger.

28. The valve insert of claim 26, wherein the valve plunger further comprises
   an entry opening for passing the pressure, and
   a radial opening for passing the pressure to the sleeve; and
   wherein the valve plunger is substantially tubular.

29. The value insert of claim 28, wherein the valve plunger further comprises a closed pressure surface opposite the entry opening for directing the pressure.

* * * * *